United States Patent [19]
Klein et al.

[11] Patent Number: 5,340,813
[45] Date of Patent: Aug. 23, 1994

[54] SUBSTITUTED AMINOALKYL XANTHINE COMPOUNDS

[75] Inventors: J. Peter Klein, Vashon; Gail Underiner, Bothell; Alistair Leigh, Edmonds, all of Wash.

[73] Assignee: Cell Therapeutics, Inc., Seattle, Wash.

[21] Appl. No.: 973,804

[22] Filed: Nov. 9, 1992

[51] Int. Cl.$^5$ .................. C07D 473/04; A61K 31/52
[52] U.S. Cl. ...................... 514/263; 544/272
[58] Field of Search ............ 544/267, 272; 514/263

[56] References Cited
U.S. PATENT DOCUMENTS

| | | | |
|---|---|---|---|
| 4,061,753 | 12/1977 | Godor et al. | 544/272 |
| 4,275,064 | 6/1981 | Bodor et al. | 544/272 |
| 4,565,817 | 1/1986 | Korbonits et al. | 544/138 |
| 4,618,612 | 10/1986 | Baglioni et al. | 544/269 |
| 5,039,666 | 8/1991 | Novick, Jr. | 514/37 |

Primary Examiner—Mukund J. Shah
Assistant Examiner—P. K. Sripada
Attorney, Agent, or Firm—Jeffrey B. Oster

[57] ABSTRACT
Compounds of the formula

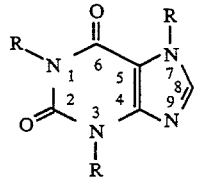

FORMULA 1 wherein each of one or two R is independently

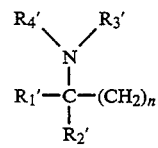

wherein n is an integer from 4 to 18, each $R_1'$ and $R_2'$ is independently H, alkyl (1–4C) or alkenyl (1–4C); and $R_3'$ and $R_4'$ are independently H or $CH_3$; and wherein the alkyl or alkenyl may be substituted by a hydroxyl, halo or dimethylamino group and/or interrupted by an oxygen atom, H or alkyl (1–4C), including resolved enantiomers and/or diastereomers and mixtures thereof. Preferably, n is from 6 to 10, $R_1'$ and $R_2'$ are independently H or methyl and $R_3'$ and $R_4'$ are H. In particular, the compounds lower elevated levels of unsaturated, non-arachidonate phosphatidic acid (PA) and diacylglycerol (DAG) derived from said PA within seconds of the primary stimulus and their contact with said cells. The modulatory effect depends on the nature of the target cell and the stimulus applied.

7 Claims, 7 Drawing Sheets

SUBSTITUTED AMINOALKYL XANTHINE COMPOUNDS

TECHNICAL FIELD OF THE INVENTION

The invention relates to a class of substituted aminoalkyl xanthine compounds that are effective agents to modulate cellular responses to stimuli. More specifically, the inventive compounds have at least one amino-containing substituent bonded to a ring nitrogen. The inventive compounds are useful antagonists to control intracellular levels of specific sn-2 unsaturated phosphatidic acids and corresponding phosphatidic acid-derived diacylglycerols which occur in response to cellular proliferative stimuli.

BACKGROUND ART

Pentoxifylline (1-(5-oxohexyl)-3,7-dimethylxanthine), abbreviated PTX, is a xanthine derivative which has seen widespread medical use for the increase of blood flow. PTX is disclosed in U.S. Pat. Nos. 3,422,307 and 3,737,433. Metabolites of PTX were summarized in Davis et al., Applied Environment Microbiol. 48:327, 1984. A metabolite of PTX is 1-(5-hydroxyhexyl)-3,7-dimethylxanthine, designated M1. M1 was also disclosed as increasing cerebral blood flow in U.S. Pat. Nos. 4,515,795 and 4,576,947. In addition, U.S. Pat. Nos. 4,833,146 and 5,039,666 disclose use of tertiary alcohol analogs of xanthine for enhancing cerebral blood flow.

Furthermore, U.S. Pat. No. 4,636,507 describes an ability of PTX and M1, to stimulate chemotaxis in polymorphonuclear leukocytes in response to a stimulator of chemotaxis. PTX and related tertiary alcohol substituted xanthines inhibit activity of certain cytokines to affect chemotaxis (U.S. Pat. No. 4,965,271 and U.S. Pat. No. 5,096,906). Administration of PTX and GM-CSF decrease tumor necrosis factor (TNF) levels in patients undergoing allogeneic bone marrow transplant (Bianco et al., Blood 76:Supplement 1 (522A), 1990). Reduction in assayable levels of TNF was accompanied by reduction in bone marrow transplant-related complications. However, in normal volunteers, TNF levels were higher among PTX recipients. Therefore, elevated levels of TNF are not the primary cause of such complications.

Therefore, there is a need in the art to discover effective therapeutic compounds that are safe and effective for human or animal administration and that can maintain cellular homeostasis in the face of a variety of inflammatory stimuli. The present invention was made in a process of looking for such compounds.

SUMMARY OF THE INVENTION

We have found that the compounds described herein can be used to maintain homeostasis of a large variety of target cells in response to a variety of stimuli. In addition, the inventive compounds and compositions are suitable for normal routes of therapeutic administration and permit effective dosages to be provided.

The invention is directed to the use of substituted xanthines containing at least one amino derivatized side chain in modulating cellular response to external or in situ primary stimuli, as well as to specific modes of administration of such compounds in effective amounts.

The inventive compounds comprise compounds and pharmaceutical compositions comprising compounds of the formula,

FORMULA 1 wherein each of one or two R is independently wherein n is an integer from 4 to 18, each $R_1'$ and $R_2'$ is independently H, alkyl (1-4C) or alkenyl (1-4C); and $R_3'$ and $R_4'$ are independently H or $CH_3$; and wherein the alkyl or alkenyl groups may be substituted by a hydroxyl, halo or dimethylamino group and/or interrupted by an oxygen atom, H or alkyl (1-4C), including resolved enantiomers and/or diastereomers, salts and mixtures thereof. Preferably, n is from 6 to 10, $R_1'$ and $R_2'$ are independently H or methyl and $R_3'$ and $R_4'$ are H.

The present invention further comprises a method for modulating an immune response or a cellular response to external or in situ primary stimuli comprising administering an effective amount of a compound of Formula 1. More specifically, the invention is directed to methods to decrease proliferation of tumor cells in response to an activated oncogene; to stimulate hematopoiesis in the presence of agents which inhibit hematopoiesis, such as chemotherapeutic agents; to suppress the activation of T-cells in the presence of antigen and the secretion of antibodies by B-cells in the presence of antigen; to suppress the activation of macrophage or endothelial cells by endotoxins, TNF, IL-1 or GM-CSF; to enhance the resistance of mesenchymal cells to tumor necrosis factor (TNF); to inhibit the proliferation of smooth muscle cells endothelial cells, fibroblasts and other cell types in response to growth factors, such as PDGF-AA, BB, FGF, EGF, etc.; to inhibit the activation of T-cells and viral replication in response to human immunodeficiency virus; to inhibit the proliferation of kidney mesangial cells m response to IL-1; to prevent suppression of Steel factor (also called stem cell factor, mast cell growth factor and kit ligand), G-CSF, oncostatin M or IL-6 in bone marrow stromal cells in response to TNF; to suppress expression of adhesion molecules in endothelial cells and suppress adhesion of inflammation cells to endothelial cells; to suppress proliferation of kidney mesangial cells in response to IL-1, mip-1α, PDGF or FGF; to prevent toxicity in kidney glomerular or tubular cells in response to cyclosporin A or amphotericin B; to prevent cytotoxic effects in gastrointestinal or pulmonary epithelial cells in response to a cytotoxic drug or radiation; to enhance the antitumor effects in tumor cells in response to a nonalkylating antitumor agent; to suppress the production of metalloproteases in synovial cells, other fibroblasts and a glomerular epithelial cell in response to inflammatory stimuli, such as TNF, IL-1 and the like, to inhibit production of osteoclast-activating factor (OAP) by osteoclasts in response to IL-1; to inhibit degranulation of mast cells and basophils in response to IgE; to modulate signal transduction of the neurotransmitters epinephrine and acetylcholine in neural pathways utilizing these transmitters, block activation of platelet activating factor in inflammation cells, block release of TNF and IL-1 in various cell types in response to inflammatory stimuli, block activation and proliferation of lymphocytes and other cell types to IL-1 and IL-2, and the like including the clinical manifestations of these cellular events, comprising administering an effective amount of a compound of Formula 1.

In still another aspect, the invention is directed to a pharmaceutical composition comprising a compound of Formula 1 and an effective amount of an agent which reduces the activity of the enzyme P-450, such as a quinolone, to increase the pharmacokinetic half-life of a compound of Formula 1.

DETAILED DESCRIPTION OF THE INVENTION

The invention is directed to a defined genus of compounds which can control cellular behavior by a particular phase of a secondary messenger pathway system (Bursten et al. J. Biol. Chem. 266:20732, 1991). The second messengers are lipids or phospholipids and use the following abbreviations:

PE = phosphatidyl ethanolamine
LPE = lysophosphoethanolamine
PA = phosphatidic acid
LPA = lysophosphatidic acid
DAG = diacylglycerol
LPLD = lysophospholipase-D
LPAAT = lysophosphatidic acid acyl transferase
PAPH = phosphatidic acid phosphohydrolase
PLA-2 = phospholipase A-2.
PLD = phospholipase D
PAA = phosphoarachidonic acid
PLA-2 = phospholipase A2
PC = phosphatidyl choline "remodeled" PA, cyclic pathway = PAA, LPA, PA and DAG intermediates substituted with L-saturated, 2-linoleoyl or 1,2-dileolyl/1,2-sn-dilinoleoyl at the indicated sn-1 and sn-2 positions.

"Classical PI Pathway" = PI, DAG, PA intermediates substituted with 1-stearoyl, 2-arachidonoyl fatty acyl side chains.

"PLD-generated PA" = PE, PC, LPA, PA and DAG intermediates substituted with, e.g., 1,2-sn-dioleoyl-, 1-alkyl, 2-linoleoyl-, and 1-alkyl, 2-docosahexaneoyl- side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as interleukin-1 or TNF) acting at a receptor on a cellular surface. An immediate detectable effect is an elevation of levels of PA and DAG. Administration of the compounds of the invention reverse this elevation.

The compounds of the invention, include inhibitors of subspecies of LPAAT in PAPH enzymes with substrate specificity for intermediates with 1,2-diunsaturated and 1-alkyl, 2-unsaturated subspecies. One representative example of such an inhibitor (although not within the genus defined by Formula 1) is PTX. PTX blocks PAPH in a specific activation pathway that does not involve PI but rather derives from a PA that is largely composed of 1,2-diunsaturated and 1-alkyl,2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH and LPAAT that relates to substrates with unsaturated fatty acids other than arachidonate in the sn-2 position, not the housekeeping forms of these enzymes that serve the PI pathway.

In Vitro Assays for Physiologic and Pharmacologic Effects of the Invention Compounds Various in vitro assays can be used to measure effects of the inventive compounds to module immune activity and have antitumor activity using a variety of cellular types. For example, a mixed lymphocyte reaction (MLR) provides a valuable screening tool to determine biological activity of each inventive compound. In the MLR, PBMCs (peripheral blood mononuclear cells) are obtained by drawing whole blood from healthy volunteers in a heparinized container and diluted with an equal volume of hanks balanced salt solution (HBSS). This mixture is layered on a sucrose density gradient, such as a Ficoll-Hypaque® gradient (specific gravity 1.08), and centrifuged at 1000×g for 25 minutes at room temperature or cooler. PBMC are obtained from a band at a plasma-Ficoll interface, separated and washed at least twice in a saline solution, such as HBSS. Contaminating red cells are lysed, such as by ACK lysis for 10 min. at 37° C., and the PBMCs are washed twice in HBSS. The final pellet of purified PBMCs are resuspended in complete medium, such as RPMI 1640 plus 20% human inactivated serum. The proliferative response of PBMC to allogeneic stimulation is determined in a two-way MLR performed in a 96-well microtiter plate. Briefly, approximately $10^5$ test purified PBMC cells in 200 µl complete medium are co-cultured with approximately $10^5$ autologous (control culture) or allogeneic (stimulated culture) PBMC cells, wherein the allogeneic cells are from HLA disparate individuals. Varying doses of compounds (drug) are added at the time of addition of cells to the microtiter plate and the cultures are incubated for 6 days at 37° C. in a 5% $CO_2$ atmosphere. At the conclusion of the incubation tritiated thymidine is added (for example 1 µCi/well of 40 to 60 Ci/mmole) and proliferation determined by liquid scintillation counting.

A thymocyte costimulator assay is conducted to evaluate the inventive compounds to inhibit activation and proliferation of thymocytes caused by stimulation with Con A and/or interleukin-1 (IL-1). Thymuses are obtained from mice (e.g., female Balb/C mice) and the thymuses removed and dissociated into culture media (e.g., RPMI 1640 without serum supplementation). The dissociated thymus tissue and cell suspension is transferred to centrifuge tubes and allowed to settle, washed with HBSS and resuspended in serum-supplemented culture media (e.g., RPMI 1640 with 10% fetal calf serum). Any contamination red cells are lysed, and viable cells resuspended and counted. Thymocytes are plated (e.g., 96-well plates at a density of $2 \times 10^5$ cells/well) and Con A, IL-1 (e.g., IL-1α) or IL-2 added to the well and the cells incubated for 4 days at 37° C. On the fourth day, the cells are pulsed with tritiated thymidine and cell proliferation determined. Inventive compounds are added approximately at the time of Con A, IL-1 or IL-2 addition.

Each inventive compound is investigated for cytotoxicity to determine appropriate doses for biological activity assays and to prevent cytotoxic reactions in in vitro assays when characterizing activity. Cells (e.g., NIH-3T3, Ras transformed 3T3 cells, malignant melanoma LD2 cells, etc.) are added to microtiter plates and drug is added about two days after plating. Cell viability is determined using a fluorescent viability stain (2',7'-bis-(2-carboroxyethyl)-5-(and -6)- carboxyfluorescein acetoxymethyl ester, BCECF excitation 488 nm and emission 525 nm) 24, 48 or 72 hours after addition of the drug.

Another assay for measuring activity of the inventive compounds involves determining PDGF (platelet derived growth factor) proliferative response using human-derived stromal cells. Human stromal cells are plated (e.g., 4000 cells per well) in defined media (e.g., 69% McCoy's, 12.5% fetal calf serum, 12.5% horse serum, 1% antibiotics, 1% glutamine, 1% vitamin supplement, 0.8% essential amino acids, 1% sodium pyrorate, 1% sodium bicarbonate, 0.4% non-essential amino acids and 0.36% hydrocortisone). One day later, the stromal cells are starved in 0.5% serum-containing media. Twenty four hours later, the cells are treated with a stimulating agent, such as PDGF-AA, PDGF-BB or basic FGF (fibroblast growth factor) with or without IL-1α or TNF, and tritiated thymidine. Cell proliferation is determined by liquid scintillation counting.

A B-cell proliferation assay determines the effect of the inventive compounds on inhibiting proliferation of stimulated B-cells, stimulated by an anti-mu antibody (40 µug/ml), IL-4 or PMA (2.5 nM). Ramos B-cell tumor cells can be incubated with a stimulating agent, an inventive compound and tritiated thymidine to measure inhibition of cell proliferation caused by the stimulating agent.

One in vitro assay measures inhibition of the relevant enzymes lysophosphatidic acid acyltransferase (LPAAT) and phosphatidic acid phosphoryl hydrolase (PAPH). The assay involves incubating of target cells with a primary stimulus (e.g., a variety of cytokines, growth factors, oncogene products, putatively therapeutic agents, irradiation, viral infection, toxins, bacterial infection and the products thereof, and any stimulus which, if not counteracted, has a deleterious effect on the target cell) in the presence or absence of an inventive compound at varying dosage levels. Target cells include, for example, subcellular entities, such as, microsomes derived from mesenchymal and/or ectodermal cells, particularly microsomes from marrow stromal cells or human or rat mesangial cells; microsomes or synaptosomes derived from bovine brain; plasma membrane-enriched microsomes or plasma membranes derived as described in Bursten et al. (J. Biol. Chem 226:20732–20743, 1991) detergent-solubilized microsomes; synaptosomes, and membranes or other cell preparations solubilized using, for example, NP-40, Miranal, SDS or other neutral detergents; and detergent-solubilized or further purified preparations of cell proteins, including the proteins LPAAT and/or PAPH. After incubation for short periods of time, cell lipids are extracted and assayed by thin layer chromatography according to standard procedures. Briefly, lipids are extracted using, for example, chloroform:methanol 2:1 (v/v), and the extracts are then subjected to HPLC as described in Bursten and Harris, Biochemistry, 30:6195–6203, 1991. A Rainin mu-Porasil column is used with a 3:4 hexane:propanol organic carrier and a 1–10% water gradient during the first 10 minutes of separation. Detection of the peaks in the elution pattern is by absorption in the range of ultraviolet which detects isolated double bonds. The relevant peaks of unsaturated PA and DAG are shown in the elution pattern. It is important to note that the assay method permits discrimination between various forms of PA and DAG so that those relevant to the pathway affected by the (R) or (S) compounds of the invention can be measured directly. Confirmation of the nature of the acyl substituents of these components is accomplished using fist-atom bombardment mass spectroscopy. Thus, the relevant unsaturated (non-arachidonic) PA and DAG subspecies may be detected. The time periods employed are 5–60 seconds after stimulation with the primary stimulus, such as a cytokine. This technique permits assessment of the levels of various lipid components as a function of time.

Compounds of the Invention

The inventive compounds comprise compounds and pharmaceutical compositions comprising compounds of the formula,

FORMULA 1 wherein each of one or two R is independently wherein n is an integer from 4 to 18, each $R_1'$ and $R_2'$ is independently H, alkyl (1–4C) or alkenyl (1–4C); and $R_3'$ and $R_4'$ are independently H or $CH_3$; and wherein the alkyl or alkenyl may be substituted by a hydroxyl, halo or dimethylamino group and/or interrupted by an oxygen atom, H or alkyl (1–4C), including resolved enantiomers and/or diastereomers, salts such as a HCl salt, and mixtures thereof. Preferably, n is from 6 to 10, $R_1'$ and $R_2'$ are independently H or methyl and $R_3'$ and $R_4'$ are H.

Those embodiments are preferred wherein a single alkyl amine substituent (e.g., R) is at position 1 of this xanthine nucleus, or where the alkyl amine substituents are at position 1 and 7. Also preferred, are those compounds of the invention wherein a single R substituent which is an amino alkyl substituent is at position 7 of the xanthine nucleus.

The remaining R substituents are independently H, alkyl (1–6C), alkenyl (1–6C) or benzyl wherein the alkyl or alkenyl substituents may be further substituted with a hydroxy group, halo, dimethylamine and/or may be interrupted by an oxygen atom. Suitable embodiments for the remaining R groups include methyl, ethyl, isopropyl, n-propyl, isobutyl, n-butyl, t-butyl, 2-hydroxyethyl, 3-hydroxypropyl, 3-hydroxy-n-butyl, 2methoxyethyl, 4-methoxy-n-butyl, 5-hydroxyhexyl, 2-bromopropyl, 3-dimethylaminobutyl, 4-chloropentyl, and the like. Particularly preferred substituents are ethyl, methyl, or H; and especially methyl or H. Particularly preferred compounds of the invention are also exemplified herein.

The compounds of the invention may be provided as enantiomeric or diastereomeric mixtures or in resolved or partially resolved forms. Standard procedures are used for resolution of optical isomers. It is contemplated that the different enantiomeric variants (e.g., stereoisomers and chiral forms) of the xanthines will have different drug activities, based upon their differential ability to inhibit PAPH and LPAAT. By an optical isomer substantially free of the corresponding enantiomer and/or diastereomers is meant at least about 85% relevant optical isomer, preferably at least about 95% relevant optical isomer and especially at least about 99% or higher relevant optical isomer, but most preferably where the amount of other optical forms is undetectable.

The present invention further comprises a pharmaceutical composition comprising one or a plurality of compounds of Formula 1 and an pharmaceutically acceptable carrier or excipient. The cells to be treated with an inventive compound or inventive pharmaceutical composition may either be contacted with the compound of the invention in vitro culture, in an extracorporeal treatment, or by administering the compound of the invention or pharmaceutical composition to a subject whose cells are to be treated.

| Illustrative compounds of the invention include: | |
|---|---|
| CT1520 | N-(5-aminohexyl) theobromine |
| CT1520.1 | dimer of CT1520 |
| CT1548 | N-(7-aminooctyl) theobromine |
| CT1557 | N-(5-methylaminohexyl) theobromine |
| CT1558 | N-(5-dimethylaminohexyl) theobromine |

Uses of the Invention Compounds and Pharmaceutical Formulations

The compounds of the invention provide a mechanism to maintain homeostasis in cells contacted by primary stimuli through mitigating the effects of these primary stimuli on the secondary signaling pathways invoked within seconds of the primary stimulus.

For example, the compounds of the invention are used in connection with patients undergoing bone marrow transplantation (BMT), regardless of whether the BMT is matched allogeneic, mismatched allogeneic, or autologous. Patients receiving autologous transplants are aided by treatment with compounds of the invention even though they do not necessarily need to be administered immunosuppressive agents, since they do not develop graft-versus-host disease (GVHD). However, the toxic effect of the chemotherapy or radiation therapy used in connection with the disease, in response to which the transplantation has been performed, constitutes a negative stimulus with regard to the patients' cells.

In general, all patients undergoing BMT require doses of chemotherapy with or without total body irradiation that exceed the lethal dose for normal bone marrow recovery. This provides the rationale for using either stored patient marrow or donor marrow to rescue the patient. In general, chemotherapy and radiation are delivered to the patient for 7–10 consecutive days before the new or stored bone marrow is infused. The day on which the marrow is given to the patient is referred to as day 0 of the transplant; previous days on which the patient received chemo/radiation are designated by negative numbers. Subsequent days are referred to by positive numerals.

The median time in which negative responses in BMT recipients occurs is within the first 100 days after transplant. Therefore, statistically, if patients survive through day 100, their chances for continued survival are significantly enhanced. Compounds of Formula 1 are able to increase the percentage of patients who survive. The percentage of fatalities within the first 100 days that is considered acceptable is 15–20% for "good risk" patients and 30–40% for "high risk". These fatalities are due to the direct effects of high doses of chemo/radiation; in addition, GVHD contributes to the death rate in allogeneic marrow recipients.

Other indications for which it is useful to administer the compounds of the invention include the presence of a tumor burden, a hormone-related disorder, a neurological disorder, an autoimmune disease, inflammation, restenosis, hypertension, unwanted immune response, viral infection, nephritis, mucositis, and various allergic responses. Prevention of allergic responses include prevention of acute allergic response and thus moderation or prevention of rhinorrhea, serious drainage, diffuse tissue edema, and generalized pruritus. Other symptoms of chronic allergic response include, as well as the foregoing, dizziness, diarrhea, tissue hyperemia, and lacrimal swelling with localized lymphocyte infiltration. Allergic reactions are also associated with leukotriene release and the distal effects thereof, including asthmatic symptoms including development of airway obstruction, a decrease in FEV1, changes in vital capacity, and extensive mucus production.

Other suitable subjects for the administration of compounds of the invention, include patients being administered toxic agents for the treatment of tumors, such as chemotherapeutic agents or irradiation therapy, as well as treatment with biological response modifiers such as IL-2 and tumor suppressing cells such as lymphokine activated killer cells (LAK) and tumor-infiltrating lymphocytes (TIL cells); patients suffering from neoplasias generally, whether or not otherwise treated including acute and chronic myelogenous leukemia, hairy cell leukemia, lymphomas, megakaryocytic leukemia, and the like; disease states caused by bacterial, fungal, protozoal, or viral infection; patients exhibiting unwanted smooth muscle cell proliferation in the form of, for example, restenosis, such as patients undergoing cardiac surgery; patients who are afflicted with autoimmune diseases, thus requiring deactivation of T and B cells, and patients who have neurological disorders.

The compounds of the invention further are able to decrease the enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

Thus, the drugs of the invention are also useful to raise the seizure threshold, to stabilize synapses against neurotoxins such as strichnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

While dosage values will vary, therapeutic efficacy is achieved when the compounds of the invention are administered to a human subject requiring such treatment as an effective oral, parenteral, or intravenous sublethal dose of about 200 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

Coadministration With a P-450 Inhibitor

The coadministration in vivo of the compounds of the invention along with an inhibitor of P-450 results in an enhanced effect due to a longer half life of the inventive compounds. This in vivo effect is due to the inhibition of a degradation pathway for the compounds of the invention; in particular with respect to dealkylation at the N7 position of the xanthine core. For example, NIH3T3-D5C3 cells can be used to compare effects of a compound of Formula 1 alone or in combination with a P-450 inhibitor by comparing transformation phenotype among control, incubation with a compound of Formula 1 alone, and coincubation of a compound of Formula 1 with the P-450 enzyme inhibitor.

Compounds that inhibit P-450 include, for example, (mg range daily dosage) propranolol (20–100), metaprolol (20–100); verapamil (100–400), diltiazem (100–400), nifedipine (60–100); cimetidine (400–2,400); ciprofloxacin (500–2000), enoxacin (500–2,000), norfloxacin (500–2000), ofloxacin (500–2,000), pefloxacin (500–2,000); erythromycin (100–1,000), troleandomycin (100–1,000); ketoconizole (100–2,000), thiabenzadole (100–1,000); isoniazid (100–1000); mexiletine (100–1,000); and dexamethasone (1–100 mg).

For combination therapy, the compounds of the invention and a P-450 inhibitors can be administered individually or in a single composition. A suitable formulation will depend on the nature of the disorder to be treated, the nature of the medicament chosen, and the judgment of the attending physician. In general, these compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

Depending on the compound of Formula 1 selected, the level of dosage can be appreciably diminished by coadministration of a P-450 inhibitor, such as the quinolone. Alternatively, a strong synergistic effect may be obtained with such a quinolone.

The invention is illustrated by the following examples which should not be regarded as limiting the invention in any way. In these examples PTX means pentoxifylline.

EXAMPLE 1

Method for synthesis of 1-(5-aminohexyl)-3,7-dimethylxanthine (CT1520)

The method described in Koziara and Zwierzak, Tetrahedron Letters 28:6513–6516,1987 was followed to make CT1520. Briefly, boron trifluoride etherate (0.06 mol) was added dropwise at 10°–30° C. to a stirred solution of 1-(5-hydroxyhexyl)-3,7-dimethylxanthine (0.05 mol) and trimethylsilylazide (0.06 mol) in pentane (50 ml). After 24 hours at room temperature the mixture was poured into 100 mls of water. The organic phase was separated, washed with a 10% solution of sodium bicarbonate, and dried over sodium sulfate. The solution of the azide in pentane was stirred at 25°–30° C., and 0.05 mol of triethylphosphite was added. Stirring was continued for 6 hours, and the solution was left at this temperature for 72 hours. Solvent was evaporated off and the iminophosphorane was dissolved in ethanol (15 mls) and treated with p-toluenesulfonic acid monohydrate (0.05 mol) and water (0.05 mol). The mixture was refluxed for eight hours, evaporated and the residue diluted with 100 mls of ether. The tosyl salt of the amine was precipitated out and was recovered by filtration. Then, 30% aqueous ammonium hydroxide (20 mls) was added to the crystals and the free amine was extracted into dichloromethane (3×15 mls), dried over sodium sulfate and the solvent evaporated to yield the free amine as a viscous oil, 0.7 g with a 50% yield.

Another method to synthesize CT1520 begins with a solution of PTX (Sigma, 1.39 g, 5.0 mmol) in methanol (50 ml). Ammonium acetate (3.85 g, 50 mmol) was added and stirred for five minutes. Sodium cyanoborohydride (0.64 g, 10 mmol) was added to this solution, followed by 3 Å molecular sieves and this reaction mixture was stirred for 24 hours. The reaction mixture was filtered to remove solids. The solids were washed with dichloromethane (50 ml) and the filtrate was washed with water (50 ml). The aqueous phase was treated with saturated ammonium chloride solution (25 ml), stirred for 15 min and then a 30% aqueous ammonium hydroxide solution added (20 ml) to make the aqueous phase basic. The basic aqueous phase was extracted with 25% ethanol/dichloromethane (3×35 ml). The combined extracts were dried with magnesium sulfate. Solvent was evaporated under vacuum to provide a product as a viscous oil (0.95 g, 3.41 mmol, 68% yield).

EXAMPLE 2

Method for synthesis of 1-(7'-aminooctyl)-3,7-dimethylxanthine (CT1548)

8-Bromo-2-octanone was used to alkylate the N1 position of theobromine as described in Example 1. The resulting 1-(2-octanone)-3,7-dimethylxanthine (5 mmol) was dissolved in 50 mls of methanol. Ammonium acetate (50 mmol) was added and the mixture was stirred for 5 minutes, vented to the outside. Sodium cyanoborohydride (10 mmol) was added, followed by 3 Å molecular sieves (3 scoops). After 24 hours of stirring, the mixture was filtered by gravity and the solids rinsed with 50 mls of dichloromethane. The combined filtrates were washed with 50 mls of water and dried with sodium sulfate, and the solvent was evaporated under vacuum. The residue was treated with 5% aqueous hydrochloride (25 mls) and then extracted with ether (2×20 mls). The aqueous layer was treated with saturated aqueous ammonium chloride solution (20 ml) and stirred for 15 minutes. Then, 30% aqueous ammonium hydroxide was added (30 mls) and the solution was extracted with 25% ethanol/dichloromethane (3×35 mls). The combined extracts were dried over magnesium sulfate and the solvents were evaporated under vacuum, providing 1.02 grams, 3.4 mmol, 68% yield of a viscous oil.

Another method to synthesize CT1548 begins with a suspension of NaH (580 mg, 24.2 mmol) in DMSO (100ml) and added theobromine (3.96 g, 22.0 mmol). After 30 min, 8-bromo-1-octene (3.96 g, 22 mmol) was added and the reaction mixture was stirred for 16 hrs at 25° C. The reaction mixture was poured into 200 ml water and extracted with dichloromethane (3×50 ml). The organic portions were combined, washed with brine (50 ml), dried (sodium sulfate) and evaporated to provide 1-(7'-octenyl)-3,7-methylxanthine as a thick white oil which solidified upon standing (6.22 g, 97%). Two grams (6.89 mmol) of 1-(7'-ocetenyl)-3,7-methylxanthine was stirred in 5 ml water/6 ml sulfuric acid for 16 hrs. Water (100 ml) was added to the mixture and extracted with dichloromethane (3×50 ml). The organic portions were combined, dried (MgSO4), and evaporated to give 1-(7'-hydroxyoctyl)-3,7dimethylxanthine as an oil which solidified upon standing (1.80 g, 85% yield). 1-(7'-hydroxyoctyl)-3,7-dimethylxanthine (1.92 g, 6.22 mmol) in 10 ml dichloromethane was added to a solution of 2,2'-bipyridinium chlorochromate (2.73 g, 9.34 mM in dichloromethane (60 ml)). The reaction mixture was stirred for 16 hrs and Celite® (1 g) was added. The reaction mixture was filtered through a pad of celite, the filtrate was evaporated to a residue. The residue was re crystallized in dichloromethane/ether to give 1.52 g of the ketone (7'-oxooctyl)-3,7-dimethylxanthine as a slightly yellowish solid in an 80% yield. 7'-oxooctyl-3,7-dimethylxanthine (192 mg, 0.63 mmol), ammonium acetate (438 mg, 6.3 mmol) and 4 Å molecular sieves (1 g) were stirred for 5 min, and NaBH3CN (79 mg, 1.26 mmol) was added. This reaction mixture was stirred for 16 hrs and was then filtered to remove the sieves. The reaction was washed with Dichloromethane to remove any byproducts. The aqueous layer was treated with saturated aqueous NH4Cl (25 ml) and concentrated NH4OH (10 ml). The mixture was extracted with 25% ethanol/Dichloromethane (3×20 ml)). The organic portions were combined, dried (MgSO4), and evaporated to give CT1548 (racemic mixture) as a purplish oil which slowly solidified upon standing (80 mg, 42% yield).

EXAMPLE 3

A Method for Synthesis of 1-(10-aminoundecyl)-3,7-dimethylxanthine 1-bromo-10-undecene is used in place of 8-bromo-2-octanone in the synthesis described in Examples 1 and 2 (first parts) for amino substituted xanthines. 1-bromo-10-undecene was converted to the ketone by a modification of the Wacker process according to the method of Tsuji Synthesis 369, 5/84.

EXAMPLE 4

This example illustrates a synthesis method for CT1557 (N-(5methylaminohexyl) theobromine). A solution of PTX (2.0g, 7.2 mmol) in methanol (50 ml) was added to methylamine hydrochloride (4.85 g, 72 mmol) and stirred for 5 min. Sodium cyanoborohydride (0.9 g, 14.4 mmol) was added and this solution was stirred for 48 hrs. This solution was treated with a saturated ammonium chloride solution (70 ml), stirred for 1 min, and then a 28% aqueous ammonium hydroxide solution (100 ml) was added. The solution was extracted with dichloromethane (3×50 ml) and the combined extracts were dried (magnesium sulfate). The solvent was evaporated to give the product as a viscous oil (2.08 g, 7.10 mmol, 98% yield).

EXAMPLE 5

This example illustrates a method to synthesize CT1558 (N-(5-dimethylaminohexyl) theobromine). A solution of PTX (2.0 g, 7.2 mmol) in methanol (50 ml) was added to dimethylamine hydrochloride (5.86 g, 72 mmol) and stirred for 5 min. Sodium cyanoborohydride (0.9 g, 14.4 mmol) was added and this solution was stirred for 42 hrs. This solution was treated with a saturated ammonium chloride solution (70 ml), stirred for 1 min, and then a 28% aqueous ammonium hydroxide solution (50 ml) was added. The solution was extracted with dichloromethane (3×40 ml) and the combined extracts were washed with water (30 ml), and dried (magnesium sulfate). The solvent was evaporated under vacuum to give the product as a viscous oil (2.20 g, 7.10 mmol, 99% yield).

EXAMPLE 6

Figure 1:
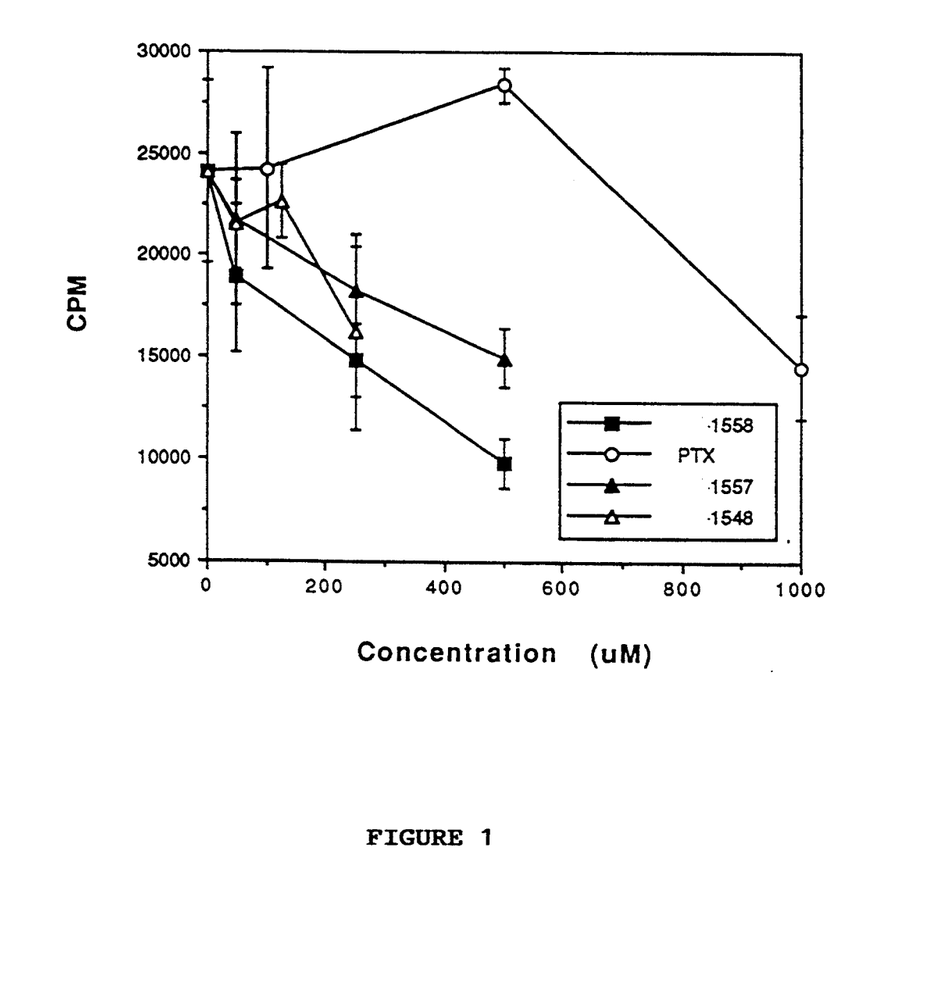
FIG. 1 shows a mixed lymphocyte reaction of PTX and three inventive compounds CT1558 (racemate N-(5-dimethylaminohexyl) theobromine), CT1557 (racemate N-(5-methylaminohexyl) theobromine), and CT1548 (racemate N-(7-aminooctyl) theobromine). The mixed lymphocyte reaction shows a proliferative response of PBMC (peripheral blood mononuclear cells) to allogeneic stimulation determined in a two-way mixed lymphocyte reaction. Each of the inventive compounds tested was more effective than PTX in this immune modulating activity assay procedure.

This example illustrates effects of CT1558, CT1557 and CT1548 on a proliferative response of PBMCs to allogeneic stimulation determined in a two-way mixed lymphocyte reaction. The two way mixed lymphocyte reaction procedure is described herein. Briefly, $10^5$ responder PBMC in 200 μl complete medium were co-cultured with 105 allogeneic cells. Autologous control cultures produced counts less than 1000. Drug was added contemporaneous with cells. The cultures were incubated for 6 days and labeled with tritiated thymidine to measure cell proliferation. Each of the inventive compounds were more effective than PTX for modulating immune activity in this assay (FIG. 1).

EXAMPLE 7

Figure 2A:
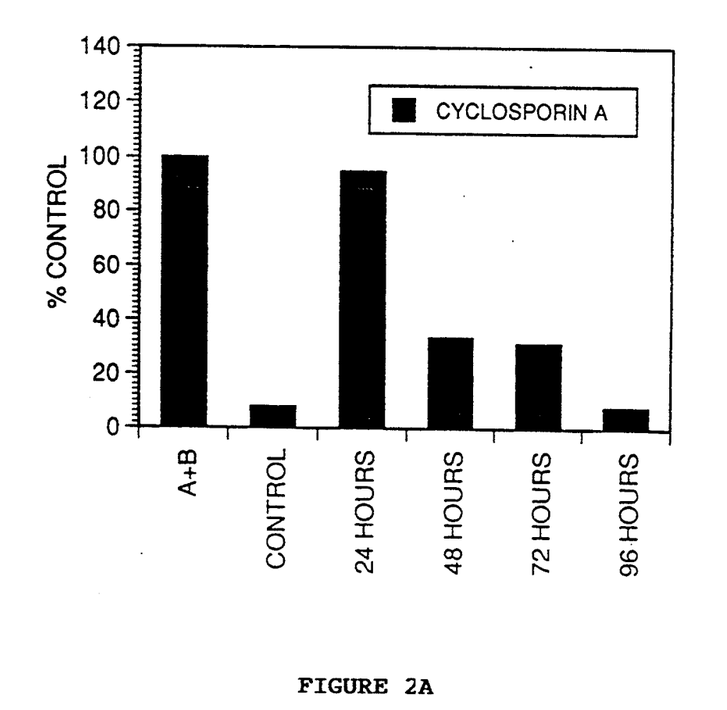
FIG. 2 shows a comparison of CT1558 and cyclosporin A (CyA) for reversibility in the mixed lymphocyte reaction (MLR) demonstrating an ability of each compound to inhibit proliferative response to a stimulus when CT1558 or CyA was in contact with the cell and allow a proliferative response to resume when the drug is removed. The data presented in FIG. 2 show that both CT1558 and CyA decreased proliferative response of mixed lymphocyte cells. However, after greater than 24 hours of treatment, CyA inhibition was irreversible whereas CT1558 inhibition was reversible.
Figure 2B:
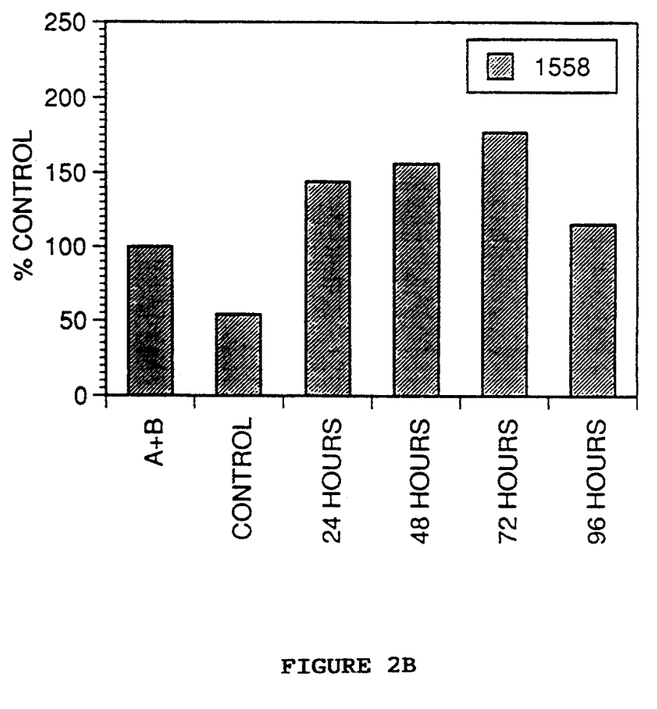

This example illustrates reversible effects of CT1558 and cyclosporin A (CyA) in a reversible mixed lymphocyte assay. This assay compares the ability of each drug to inhibit the proliferative response when the drug is in contact with cells and to allow the proliferative response to resume following drug removal. The culture were treated with 350 μg CT1558 or 3.3 μg/ml cyclosporin A continuously for 6 days prior to pulsing with tritiated thymidine. Alternatively, the cultures were treated with drug for 24, 48, 72, or 96 hrs prior to washing and resuspending in drug-free media and then pulsed with tritiated thymidine. The results in FIG. 2 indicate that CT1558 and CyA decrease the proliferative response. However, CyA inhibition is irreversible whereas CT1558 inhibition is reversible.

EXAMPLE 8

Figure 3:
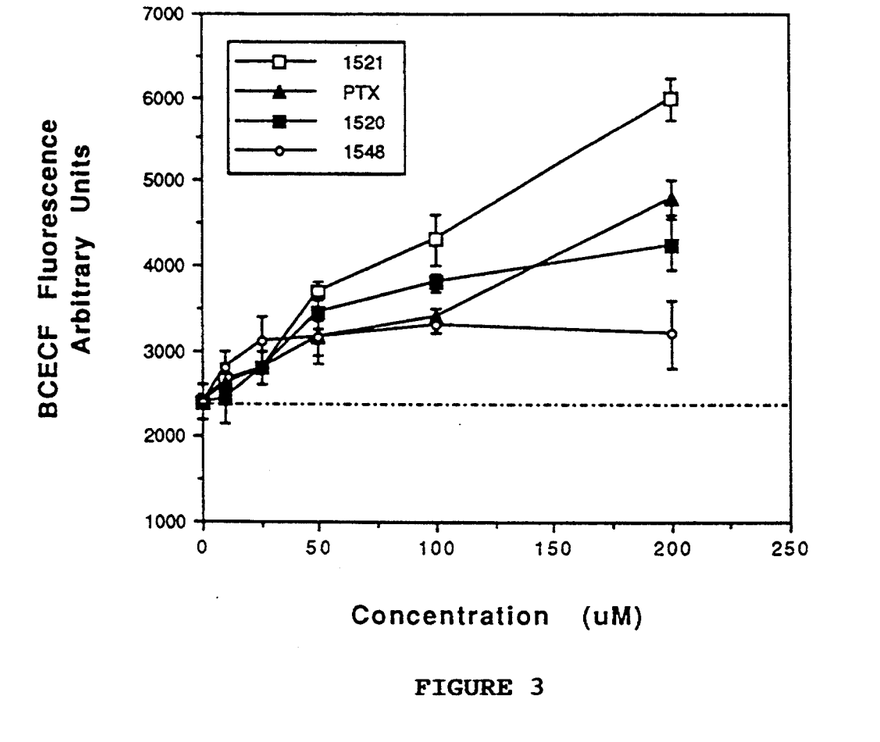
FIG. 3 shows an effect of CT1520 (racemate of N-(5-aminohexyl) theobromine), CT1548 and CT1521 (an oxime compound not within the scope of Formula 1) for protection of L929 cells from treatment with a toxic level of TNF (tumor necrosis factor, 300 ng/ml). For comparison, the results with PTX and another compound are also shown. The most potent results were seen for CT1520 and CT1548, both compounds are within the scope of Formula 1. This is an in vitro predictive model for treatment and prevention of septic shock.

This example illustrates the effects of CT1520, CT1548, CT1521 and PTX for protection of mouse L929 cells from cytotoxic effects of TNF. This procedure is an in vitro septic shock model. L929 cells ($10^5$/well) were treated with 300 ng/ml of human TNF with or without drug (added one hour prior to TNF addition) at concentrations shown in FIG. 3. One day later the cells were stained for viability using BCECF and fluorescence analyzed for viability using a Milipore fluorescence plate reader. The results shown in FIG. 3 illustrate that the most potent cytoprotective effects were seen with CT1520 and CT1548.

EXAMPLE 9

Figure 4:
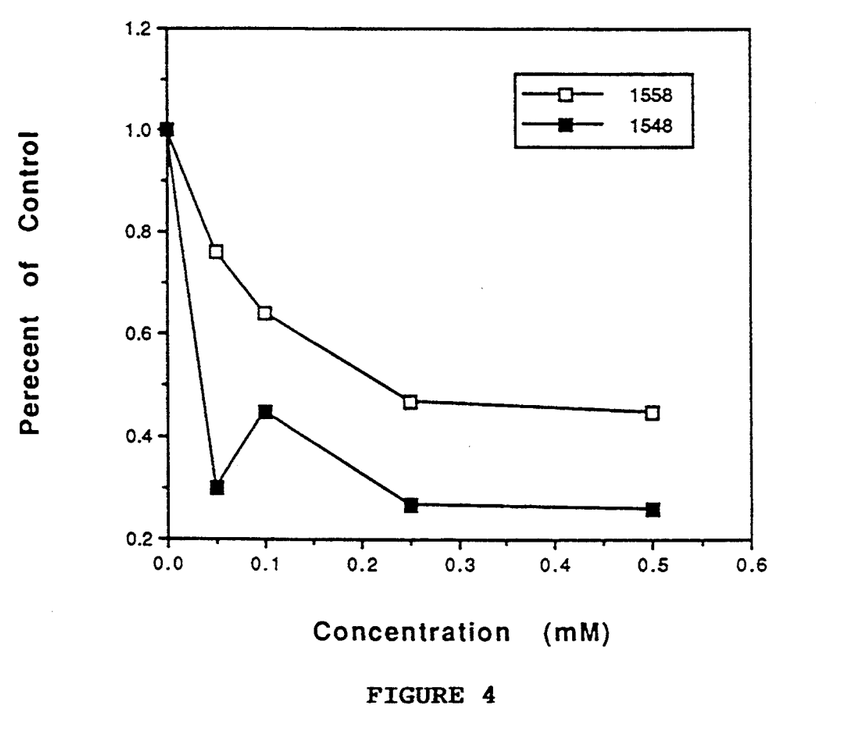
FIG. 4 shows the effects of CT1558 and CT1548 on PDGF-induced (platelet derived growth factor) proliferation in human stromal cells. Background counts were approximately 10% of control levels.

This example illustrates the effects of CT1548 and CT1558 on inhibition of PDGF-induced proliferation in human stromal cells. Human stromal cells were starved in serum-free media for 24 hours and then stimulated with 50 ng/ml PDGF-BB. The drugs were added at various concentrations one hour prior to PDGF stimulation. Tritiated thymidine was added at the time of PDGF stimulation and pulsed for 24 hours. Cells were harvested and cell proliferation measured (FIG. 4). Background counts (i.e., starved cells) were about 10% of control levels.

EXAMPLE 10

Figure 5:
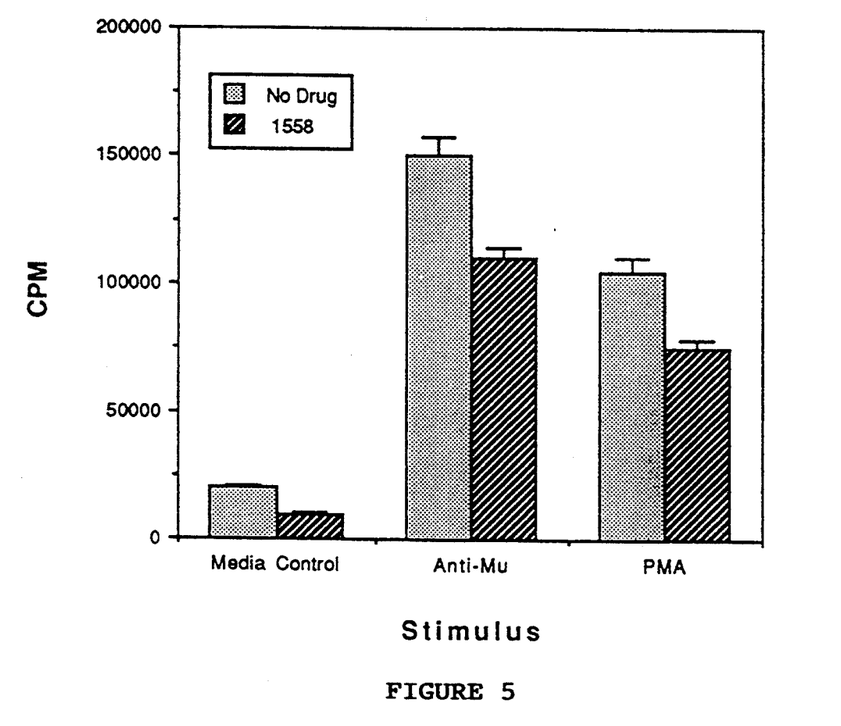
FIG. 5 shows the effect of CT1558 to inhibit proliferation of a Ramos B-cell tumor line after stimulation with either an anti-mu antibody or PMA (phorbol myristic acid). CT1558 inhibited some of the proliferative response to anti-mu and PMA.

This example illustrates the effects of CT1558 (250 μμολ) to inhibit B cell proliferation. Ramos B-cell tumor cells were treated with CT1558 for one hr prior to stimulation with anti-mu antibody or PMA (5nM). One day later the cells were pulsed with tritiated thymidine and proliferation determined (FIG. 5). CT1558 inhibited the proliferative response.

EXAMPLE 11

Figure 6:
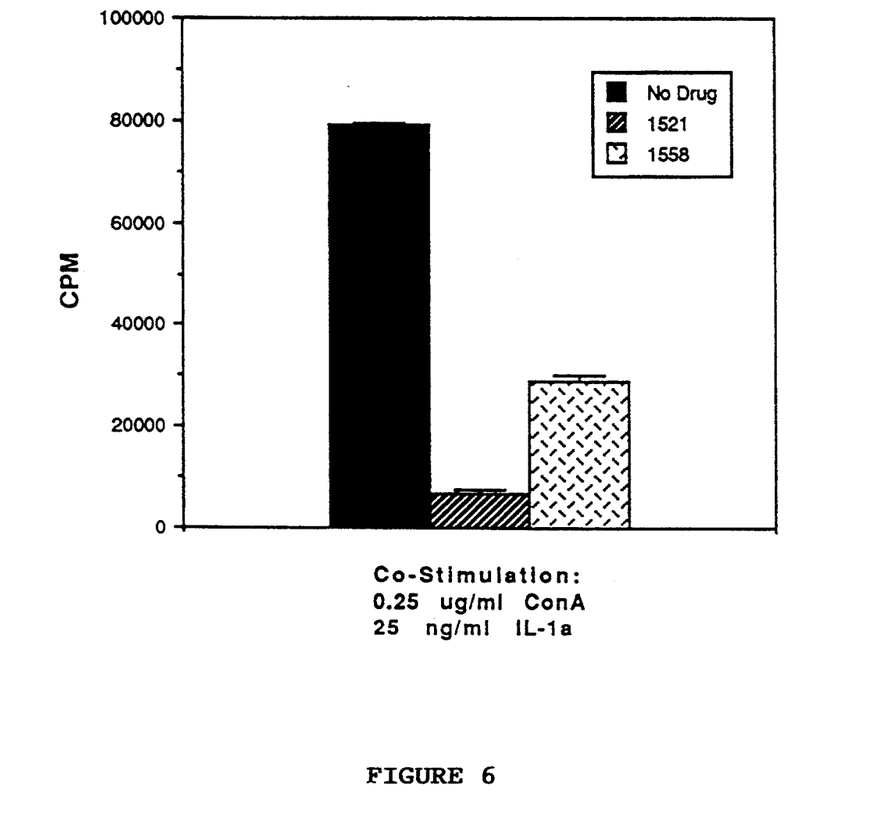
FIG. 6 shows a thymocyte proliferation assay wherein thymocyte proliferation is stimulated by Con A and IL-1α. Both CT1521 and CT1558 inhibited proliferation in thymocytes.

This example illustrates the effects of CT1521 and CT1558 on thymocyte proliferation stimulated by IL-1 or Con A. The data are shown in FIG. 6. Drugs were added 2 hrs prior to stimulation. Both drugs inhibited the proliferation of thymocytes.

We claim:

1. A compound of the formula:

FORMULA 1 wherein at least one R is wherein n is an integer from 4 to 18, each $R_1'$ and $R_2'$ is independently H, alkyl (1-4C) or alkenyl (1-4C); and $R_3'$ and $R_4'$ are independently H or $CH_3$; and wherein the alkyl or alkenyl may be substituted by a hydroxyl, halo or dimethylamino group and/or interrupted by an oxygen atom, H or alkyl (1-4C), and the other R is H or $CH_3$, including resolved enantiomers and/or diastereomers, salts, and mixtures thereof.

2. The compound of claim 1 wherein the R is at position 1 of the xanthine ring.

3. The compound of claim 1 wherein one $R_4'$ is H and $R_3'$ is methyl.

4. The compound of claim 3 wherein each R' is methyl or H.

5. The compound of claim 1 wherein n is 3-12.

6. A pharmaceutical composition comprising a compound selected from the group consisting of N-(5-aminohexyl) theobromine, dimer of N-(5-aminohexyl) theobromine, N-(7-aminooctyl) theobromine, N-(5-methylaminohexyl) theobromine, N-(5-dimethylaminohexyl) theobromine, and combinations thereof, and a pharmaceutically acceptable excipient.

7. A pharmaceutical composition comprising the compound of claim 1 in admixture with at least one pharmaceutically acceptable excipient.

* * * * *